(12) United States Patent
Yeh

(10) Patent No.: US 8,542,351 B2
(45) Date of Patent: Sep. 24, 2013

(54) COATING INSPECTION DEVICE

(75) Inventor: Shi-Hsien Yeh, Yun-lin Hsien (TW)

(73) Assignee: NIKE, Inc., Beaverton, OR (US)

( * ) Notice: Subject to any disclaimer, the term of this patent is extended or adjusted under 35 U.S.C. 154(b) by 148 days.

(21) Appl. No.: 13/223,934

(22) Filed: Sep. 1, 2011

(65) Prior Publication Data

US 2013/0057849 A1 Mar. 7, 2013

(51) Int. Cl.
*G02C 1/00* (2006.01)
(52) U.S. Cl.
USPC .............................. 356/51; 351/158; 362/105
(58) Field of Classification Search
USPC .......... 356/51, 239.2, 239.7, 240.1; 351/158, 351/159.03; 362/105
See application file for complete search history.

(56) References Cited

U.S. PATENT DOCUMENTS

| | | | |
|---|---|---|---|
| 2,320,842 A | 6/1943 | Arnold et al. | |
| 5,331,169 A | 7/1994 | Tanaka et al. | |
| 6,361,194 B1 | 3/2002 | Evans et al. | |
| 6,762,419 B1 | 7/2004 | Kranz | |
| 7,008,074 B1 * | 3/2006 | Halm | 362/105 |
| 7,105,834 B2 | 9/2006 | Angal et al. | |
| 7,145,649 B2 | 12/2006 | Brass | |
| 7,234,831 B1 | 6/2007 | Hanley | |
| 7,607,775 B2 | 10/2009 | Hermanson et al. | |
| 7,784,960 B2 | 8/2010 | Lahtinen | |
| 7,787,111 B2 | 8/2010 | Kim et al. | |
| 8,007,101 B1 * | 8/2011 | Wang | 351/158 |
| 8,152,330 B2 * | 4/2012 | Waters | 362/200 |
| 2006/0012974 A1 * | 1/2006 | Su | 362/105 |
| 2006/0197905 A1 | 9/2006 | Lu | |
| 2007/0013865 A1 * | 1/2007 | Jordan | 351/158 |
| 2007/0042139 A1 | 2/2007 | Cooper et al. | |
| 2010/0260926 A1 | 10/2010 | Wolfe et al. | |
| 2010/0302502 A1 * | 12/2010 | Ahn | 351/158 |

FOREIGN PATENT DOCUMENTS

CN 201600520 10/2010

OTHER PUBLICATIONS

Notification of Grant of Patent Right for Utility Model for Chinese Patent Application No. 201220443394.4, issued Mar. 7, 2013.
First Notification of Rectification for Chinese Patent Application No. 201220443394.4, issued Dec. 20, 2012.
Response to First Notification of Rectification for Chinese Patent Application No. 201220443394.4 as filed on Feb. 6, 2013.

* cited by examiner

*Primary Examiner* — Layla Lauchman
(74) *Attorney, Agent, or Firm* — Plumsea Law Group, LLC

(57) ABSTRACT

A coating inspection device for inspecting an object after a coating material has been applied is disclosed. The coating inspection device may include a pair of eyeglasses worn on a person's face, resting on the person's ears and nose. The eyeglasses may include a frame member having a first side and a second side opposite the first side. A set of lenses may be disposed within the frame member. At least one light source may be disposed on the frame member. The ultraviolet light source may be moveable to adjust the direction in which the ultraviolet light source emits light. A switch may be disposed on the frame.

21 Claims, 6 Drawing Sheets

COATING INSPECTION DEVICE

BACKGROUND

The game of golf is an increasingly popular sport at both amateur and professional levels. A wide range of technologies related to the manufacture and design of golf balls are known in the art. For instance, a method of manufacturing golf balls involves spraying golf balls with coating material. Occasionally, the coating material is not applied evenly on the golf balls. It would be advantageous to be able to check the evenness of the coating material on the golf balls.

SUMMARY

In one aspect, an apparatus for inspecting a coating is disclosed. The apparatus may include a frame member having a first side and a second side opposite the first side. The frame member may be configured to be worn on a person's face and to receive a set of lens. The set of lens may be disposed within the frame member. The at least one ultraviolet light source may be disposed on the first side of the frame member. A switch may be disposed on the frame member. The switch may be configured to turn on the at least one ultraviolet light source when the frame member is worn by a person and to turn off the at least one ultraviolet light source when the frame member is not worn by a person.

In another aspect, the switch may include an actuator configured to open and close the switch. The actuator may be disposed on the second side of the frame member and configured to be displaced from a first position to a second position by a person's face when the coating inspection device is worn by the person. The second position may close the switch.

In another aspect, the actuator may have a lever disposed on the second side of the frame member. The lever may be configured to be biased outwardly in the first position and to be displaced toward the second side in the second position.

In another aspect, the actuator may comprise a button disposed on the second side. The button may be configured to be biased outwardly in the first position and to be displaced toward the second side in the second position.

In another aspect, the frame member may include a hollow compartment and the switch may be disposed within the hollow compartment.

In another aspect, the at least one ultraviolet light source may be disposed on the first side of the frame member above the lenses.

In another aspect, the at least one ultraviolet light source may comprise a plurality of ultraviolet light sources.

In another aspect, an apparatus for inspecting a coating is disclosed. The coating inspection device may include a frame member having a first side and a second side opposite the first side. The frame member may be configured to be worn on a person's face and to receive a set of lenses. A set of lenses may be disposed within the frame member. A first temple member and a second temple member may both be disposed on the second side of the frame member. The at least one ultraviolet light source may be disposed on the first side of the frame member. The at least one ultraviolet light source may be configured to be moved from a first position to a second position to adjust the direction in which the at least one ultraviolet light source is directed. Electrical components may be associated with the at least one ultraviolet light source. A switch may be disposed on the frame member.

In another aspect, the at least one ultraviolet light source may include a plurality of ultraviolet light sources each configured to be independently moved to direct light in a plurality of directions.

In another aspect, the at least one ultraviolet light source may be connected to the frame member by a wire. The wire may be configured to be bent to move the at least one ultraviolet light source from the first position in which the ultraviolet light source may be directed at a first angle to the second position in which the ultraviolet light source may be directed at a second angle.

In another aspect, the at least one ultraviolet light source may be connected to the frame member by a hinged member. The hinged member may be configured to pivot with respect to the first side to move the at least one ultraviolet light source from the first position in which the ultraviolet light source may be directed at a first angle to the second position in which the ultraviolet light source may be directed at a second angle.

In another aspect, the hinged member including a ball disposed within an opening in the frame member, the ball being configured to pivot within the opening.

In another aspect, the frame member may include a hollow compartment configured to house the electrical components.

In another aspect, the set of lenses may be ultraviolet resistant lenses.

In another aspect, the first temple member may include a shielding portion proximate the second side.

In another aspect, a method of inspecting a coating on a golf ball is disclosed. The method may include turning on at least one ultraviolet light source by placing a coating inspection device on a person's face. The coating inspection device may include a frame member having a first side and a second side opposite the first side. At least one ultraviolet light source may extend from the first side. A set of lenses may be disposed within the frame member. The method may also include viewing a golf ball through set of lenses while the ultraviolet light source is on.

In another aspect, the method of inspecting a coating on a golf ball may include adjusting the direction in which ultraviolet light is emitted from the ultraviolet light source by moving the ultraviolet light source from a first position to a second position.

In another aspect, the step of turning on the at least one ultraviolet light source may include pressing a switch toward the second side with the person's face.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
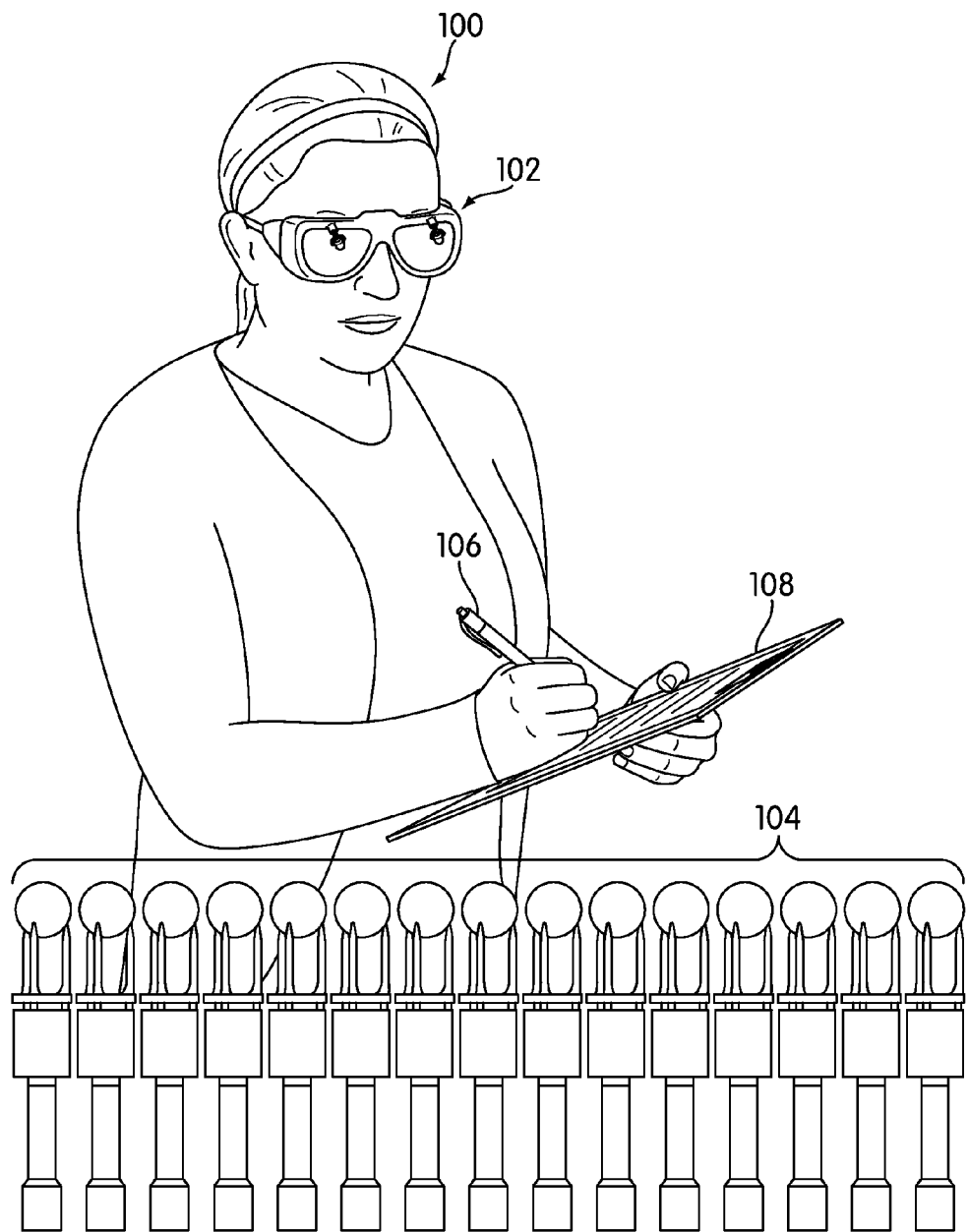
FIG. 1 illustrates a person wearing an exemplary embodiment of a coating inspection device while inspecting golf balls after coating material has been applied to the golf balls.
Figure 2:
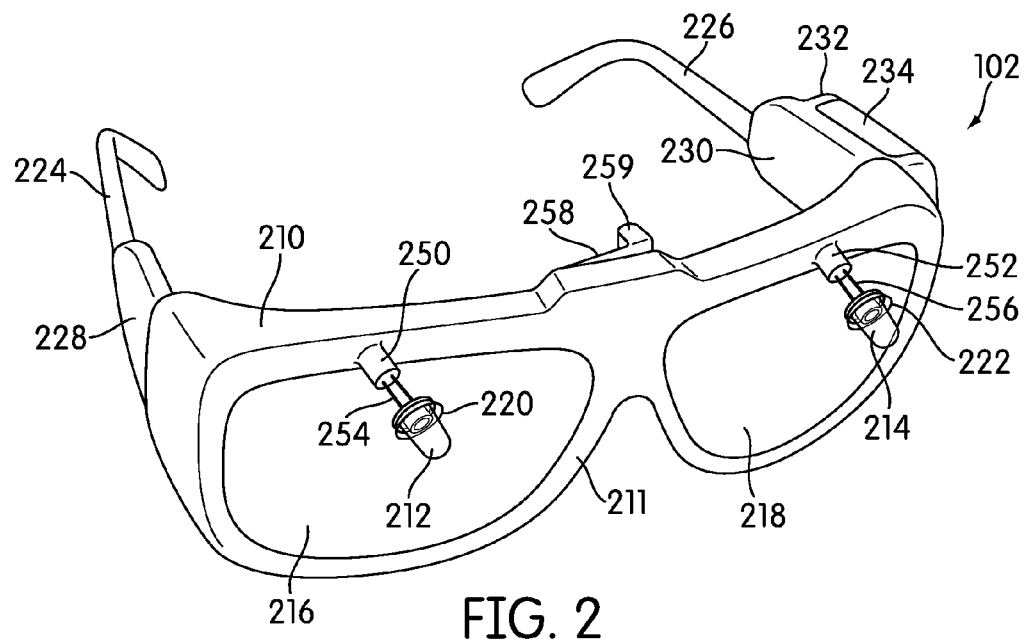
FIG. 2 is a front perspective view of the coating inspection device of FIG. 1.
Figure 3:
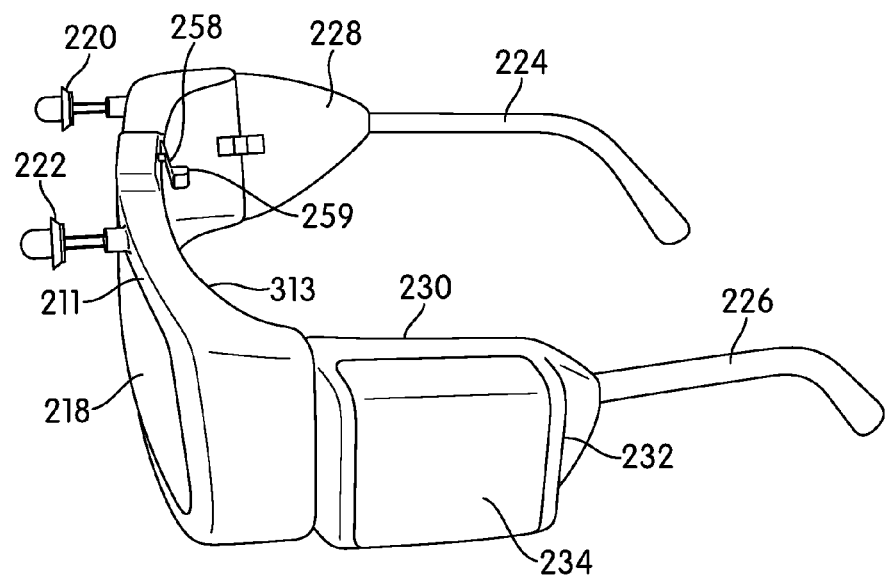
FIG. 3 is a side perspective view of the coating inspection device of FIG. 1.

FIG. 1 illustrates a person 100 wearing an exemplary embodiment of a coating inspection device 102 while inspecting golf balls 104 after coating material has been applied to golf balls 104. In some embodiments, coating inspection device 102 may include a pair of eyeglasses worn on a person's face, resting on the person's ears and nose. In some embodiments, the coating inspection device may include a pair of goggles. As described in more detail below with reference to FIG. 6, coating inspection device 102 may allow a user to see imperfections, including, for example, unevenness, in the coating of a golf ball. FIG. 1 illustrates how person 100 may inspect multiple golf balls while wearing coating inspection device 102. Because coating inspection device 102 may be worn on a person's face, person 100 may have her hands free to hold other objects and to perform other tasks. For example, as shown in FIG. 1, person 100 may hold a pen 106 and a clipboard 108 to write notes while inspecting golf balls 104. Coating inspection device 102 may be used alone without any other apparatus to inspect golf balls 104. Consequently, person 100 may inspect golf balls 104 by just looking at golf balls 104 while wearing coating inspection device 102. Moreover, due to the fact that coating inspection device 102 may be used without any other apparatus, golf balls 104 need not be relocated for inspection. While the exemplary embodiments show the coating inspection device being used to inspect the coating of golf balls, it is understood that the coating inspection device may be used to inspect the coating applied to other types of objects.

FIGS. 2-5 show detailed views of coating inspection device 102. In some embodiments, coating inspection device 102 may include a frame member 210, a first ultraviolet light source 212, a second ultraviolet light source 214, a first lens 216, and a second lens 218. In some embodiments, frame member 210 may include a first side 211 and a second side 313, shown in FIG. 3, opposite first side 211. A first temple member 224 and a second temple member 226 may both be attached to second side 313. In some embodiments, first temple member 224 and second temple member 226 may both be configured to rest on a wearer's ears. In some embodiments, frame member 210 may be configured to rest on a wearer's nose.

First ultraviolet light source 212 and second ultraviolet light source 214 may be disposed on first side 211 of frame member 210. First ultraviolet light source 212 and second ultraviolet light source 214 may be configured to illuminate objects in the presence of ultraviolet rays emitted from the ultraviolet light sources. While two ultraviolet light sources are shown in the exemplary embodiments, coating inspection device 102 may include any number of ultraviolet light sources. For example, in some embodiments, coating inspection device 102 may include one ultraviolet light source. In other embodiments, coating inspection device 102 may include ten ultraviolet light sources. The number of ultraviolet light sources may be selected based upon a variety of factors. For example, the number of ultraviolet light sources may be selected based on the amount of ultraviolet light best suited to inspect the coating of golf balls. In some embodiments, the number of ultraviolet light sources may be selected based on the strength of the light emitted by the ultraviolet light sources. In some embodiments, additional non-ultraviolet light source(s) may be added near the ultraviolet light sources.

First ultraviolet light source 212 and second ultraviolet light source 214 may include any known type of device capable of emitting ultraviolet rays. For example, in some embodiments, the ultraviolet light sources may include incandescent ultraviolet light bulbs, ultraviolet light emitting diodes, or ultraviolet compact fluorescent lamps. In some embodiments, identical ultraviolet light sources may be used. For example, first ultraviolet light source 212 and second ultraviolet light source 214 may be both ultraviolet light emitting diodes. In some embodiments, different types of ultraviolet light sources may be used. For example, first ultraviolet light source 212 may include an ultraviolet light emitting diode and second ultraviolet light source 214 may include an ultraviolet compact fluorescent lamp. The types of ultraviolet light sources used may be selected based on a variety of factors. For example, in some embodiments, the types of ultraviolet light sources may be selected based on the type of electrical power source used to power the ultraviolet light sources. In some embodiments, the types of ultraviolet light sources may be selected based on the lifespan of the ultraviolet light sources. In some embodiments, first ultraviolet light source 212 may include a first reflector 220 and second ultraviolet light source 214 may include a second reflector 222. First reflector 220 and second reflector 22 may include a concave shape to help focus the ultraviolet light rays.

In the exemplary embodiment shown in FIGS. 1-6, first ultraviolet light source 212 may be placed above the center region of first lens 216 and second ultraviolet light source 214 may be placed above the center region of second lens 218. In some embodiments, the ultraviolet light sources may be placed in other locations. The placement of the ultraviolet light sources may be selected based upon a variety of factors. For example, the placement of the ultraviolet light sources may be selected based on the shape and design of the frame member. In some embodiments, the placement of the ultraviolet light sources may be selected based on the type and/or number of ultraviolet light sources used. In some embodiments, the ultraviolet light sources may be placed on one or both of the temple members, in place of or in addition to the ultraviolet light sources disposed on the frame member.

In some embodiments, first lens 216 and second lens 218 may include transparent lenses. In some embodiments, first lens 216 and second lens 218 may include shaded, polarized, and/or colored lenses, particularly lenses which may enhance the viewing of objects with ultraviolet light. In some embodiments, first lens 216 and second lens 218 may include ultraviolet resistant lenses to protect the wearer's eyes from ultraviolet rays emitted from ultraviolet light sources. For example, in some embodiments, first lens 216 and second lens 218 may be treated with an ultraviolet resistant coating or the lenses may be treated with an invisible dye that blocks ultraviolet light. In some embodiments, first lens 216 and second lens 218 may be made of an ultraviolet resistant material, such as polycarbonate or a high index plastic. In some embodiments, first lens 216 and second lens 218 may include a single lens.

While the exemplary embodiment includes two lenses, some embodiments may include only a single lens. In some embodiments, coating inspection device 102 may include more than two lenses. For example, coating inspection device 102 may include four lenses. The number of lenses may be selected based on a variety of factors. For example, the number of lenses may be selected based on the number of other components and/or the placement of other components.

In some embodiments, frame member 210 may be configured to shield a wearer's eyes from ultraviolet light rays in the spaces between the frame member and the wearer's face. To accomplish this goal, frame member 210 may be sized and shaped to minimize the space between frame member 210 and the wearer's face when frame member 210 is worn. In some embodiments, first temple member 224 and a second temple member 226 may both be hingedly attached to second side 313 so that coating inspection device 102 may be folded up into a compact storage position. In some embodiments, first temple member 224 may include a first shielding portion 228 and second temple member 226 may include a second shielding portion 230. The shielding portions may be configured to protect the wearer's eyes from ultraviolet rays emitted from the ultraviolet light source. In some embodiments, first shielding portion 228 may be located adjacent to first lens 216. In some embodiments, second shielding portion 230 may be located adjacent to second lens 218. In some embodiments, the shielding portions may include a widened section of the temple members. In some embodiments, first shielding portion 228 and second shielding portion 230 may have the same shape. In some embodiments, first shielding portion 228 and second shielding portion 230 may have different shapes. The size and shape of the shielding portions may be selected based on a variety of factors. For example, in some embodiments, the size and shape of the shielding portions may be selected based on the shape and design of frame member 210. In some embodiments, the size and shape of the shielding portions may be selected based on the placement, size, and/or type of ultraviolet light sources. In some embodiments, the size and shape of the shielding portions may be selected based on the number of ultraviolet light sources.

In some embodiments, second shielding portion 230 may include a hollow compartment 232 for housing an electrical power source 536 for powering the ultraviolet light sources. (Electrical power source 536 is shown and discussed in more detail below with reference to FIG. 5.) In some embodiments, hollow compartment 232 may include a removable closure 234 configured to allow access to the inside of hollow compartment 232. For example, removable closure 234 may be removed to change the electrical power source. In some embodiments, first shielding portion 228 may include a hollow compartment in place of or in addition to hollow compartment 232. For example, in some embodiments, first shielding portion 228 and second shield portion 230 may both include hollow compartments for housing electrical power sources. In such an embodiment, both hollow compartments may house one or more electrical power sources. In some embodiments, the size and shape of the shielding portions may be selected based on the size and shape of hollow compartment(s). In some embodiments, the size and shape of the hollow compartment(s) may be selected based on the size and shape of the electrical power source(s) housed within the hollow compartment(s).

In some embodiments, frame member 210 may include a hollow compartment 538 configured to house electrical components (shown in hidden lines in FIG. 5) associated with the ultraviolet light sources. For example, as shown in FIG. 5, hollow compartment 538 may be configured to house a first wire 540, a second wire 542, a third wire 544, a fourth wire 546, and a switch 548. In the exemplary embodiment shown in FIGS. 1-6, hollow compartment 538 may be located above the lenses. In some embodiments, a hollow compartment may be located in other parts of frame member 210. For example, a hollow compartment may be located underneath the lenses. The location of the hollow compartment may be selected based on a variety of factors. For example, in some embodiments, the location of the hollow compartment may be selected based on the location of the ultraviolet light sources. In some embodiments, the location of the hollow compartment disposed within the frame member may be selected based on the location of the hollow compartment(s) disposed within the temple member(s) for housing the electrical power source(s). In some embodiments, the hollow compartment disposed within the frame member may be configured to house electrical components associated with the ultraviolet light sources, including also the electrical power source. In some embodiments, one or more hollow compartments may be provided in the temple member(s) to house the electrical components, including the electrical power source.

The electrical components associated with the ultraviolet light sources may include an electrical power source and provisions for putting ultraviolet light sources in electrical communication with the electrical power source. The electrical power source may include any known device or component capable of supplying electrical energy to the ultraviolet light sources. For example, the electrical power source may include one or more batteries or a solar power device. In some embodiments, the electrical power source may be rechargeable or non-rechargeable. In the exemplary embodiment shown in FIG. 5, electrical power source 536 may include a 9 Volt battery. The electrical power source may be selected based on a variety of factors. For example, in some embodiments, the electrical power source may be selected based on the type of ultraviolet light source used. In some embodiments, the electrical power source may be selected based on the weight, size (such as AA, AAA, C, D, mercury battery, or any other commercially available type), lifespan, and/or the cost of the electrical power source.

In some embodiments, the ultraviolet light sources may be put in electrical communication with the electrical power sources wirelessly by any known technology. In some embodiments, the electrical components may include wires for putting ultraviolet light sources in electrical communication with an electrical power source. For example, as shown in the exemplary embodiment of FIGS. 1-6, the wires may include first wire 540, second wire 542, third wire 544, and fourth wire 546, shown in FIG. 5. First wire 540, second wire 542, third wire 544, and fourth wire 546 may include an insulative coating to prevent the wires from shorting. In some embodiments, a switch may be provided to shut the flow of electrical energy from the electrical power source to the ultraviolet light sources on and off. The switch may include any known type of switch suitable to shut the flow of electrical energy from the electrical power source to the ultraviolet light sources on and off, such as a single pole, single throw switch, dingle pole, double throw switch, single pole changeover switch, double pole switch, single throw switch, double pole, double throw switch, double pole changeover switch, a circuit breaker switch, mercury switch, toggle switch, DIP switch, momentary switch, push-button switch, rocker switch, surface mount switch, reed switch, rocker switch, wafer switch, logic gate, or the like. The type of switch may be selected based on a variety of factors. For example, the type of switch may be selected based on the number of ultraviolet light sources. In some embodiments, the type of switch may be selected based on the type of ultraviolet light sources used and/or the type of electrical circuitry used. For example, as shown in the exemplary embodiment of FIGS. 1-6, switch 548 may be provided within hollow compartment 538.

The number of wires and the circuitry made with the wires may be selected based on a variety of factors. For example, the number of wires and the circuitry made with the wires may be selected based on the type of switch used, the shape of frame member 210, or the location of the electrical power source. As shown in FIG. 5, first wire 540 may be connected to first ultraviolet light source 212 and switch 548. Second wire 542 may be connected to second ultraviolet light source 214 and switch 548. Third wire 544 may be connected to switch 548 and electrical power source 536. Fourth wire 546 may be connected to second ultraviolet light source 214 and electrical power source 536. When switch 548 is closed, all of the wires and the ultraviolet light sources may be in electrical communication with electrical power source 536. Thus, when switch 548 is closed, electrical power source 536 may supply power to the ultraviolet light sources. When switch 548 is open, the connection between the wires may be broken so that the ultraviolet light sources are no longer in electrical communication with the electrical power source. Thus, when switch 548 is open, electrical power source 536 may not supply power to the ultraviolet light sources.

In some embodiments, the switch may include an actuator configured to open and close the switch. In some embodiments, the actuator may be configured to close the switch when the coating inspection device is worn by a person. In some embodiments, the actuator may be positioned so that the actuator contacts a person's face when the person is wearing the coating inspection device. In some embodiments, the actuator may be displaced from a first position to a second position when the actuator contacts a wearer's face. In some embodiments, such a displacement may close the switch. The exemplary embodiment of FIGS. 1-6 illustrates how the actuator may be a lever 258. Lever 258 may be connected to an outer body of switch 548 at pivot point 460. In some embodiments, lever 258 may be located on the outside of frame member 210. In some embodiments, lever 258 may protrude through an opening in frame member 210 so that lever may be connected to an outer body of switch 548 located within hollow compartment 538. In some embodiments, lever 258 may include one end extending from switch 548 and a free end opposite the end extending from switch 548. In some embodiments, lever 258 may include a component configured to contact a wearer's face at the free end. For example, in the exemplary embodiment shown in FIGS. 1-6, lever 258 may include a nub 259 for assisting in automatic activation, as discussed further herein.

Figure 4:
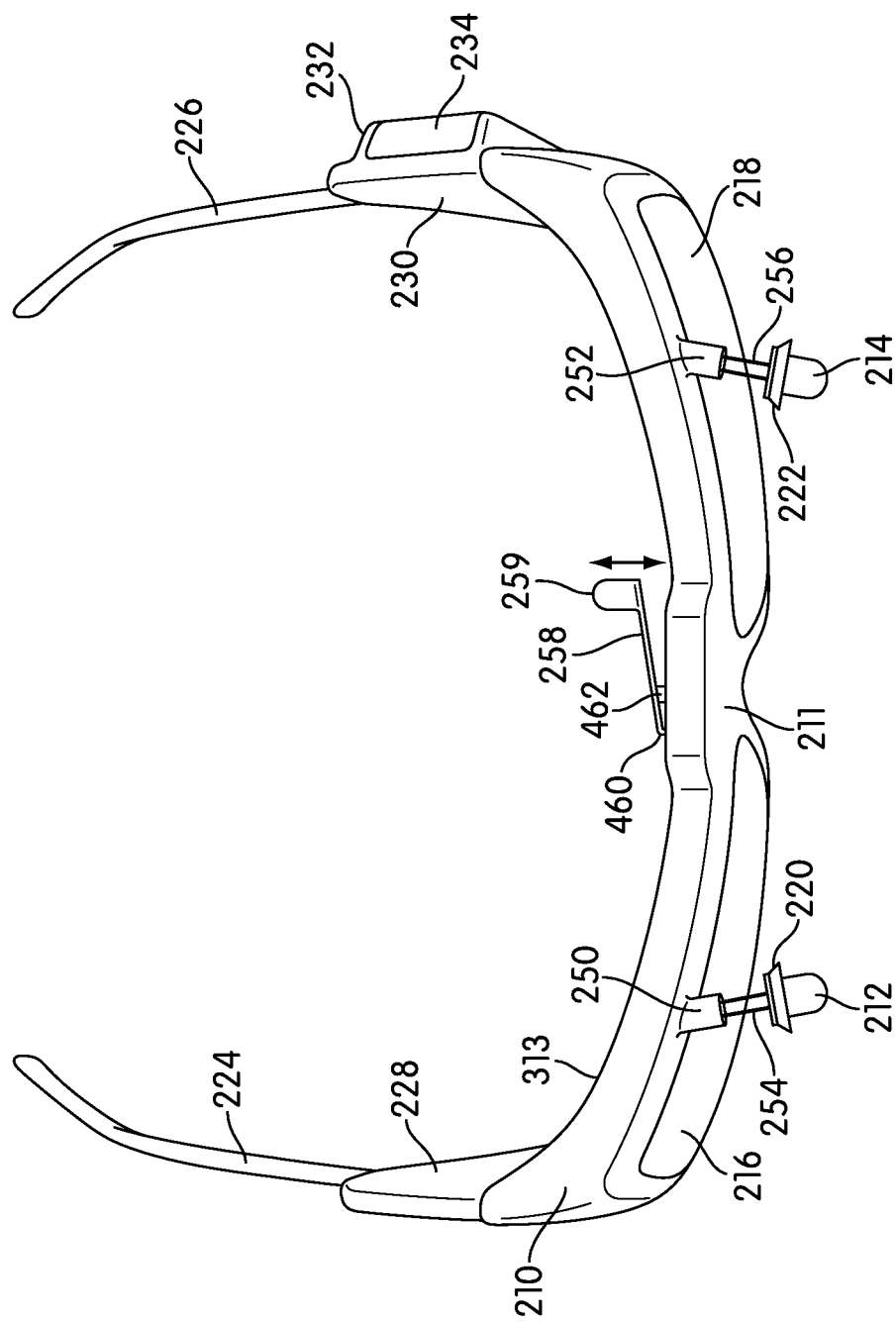
FIG. 4 is a top view of the coating inspection device of FIG. 1.
Figure 5:
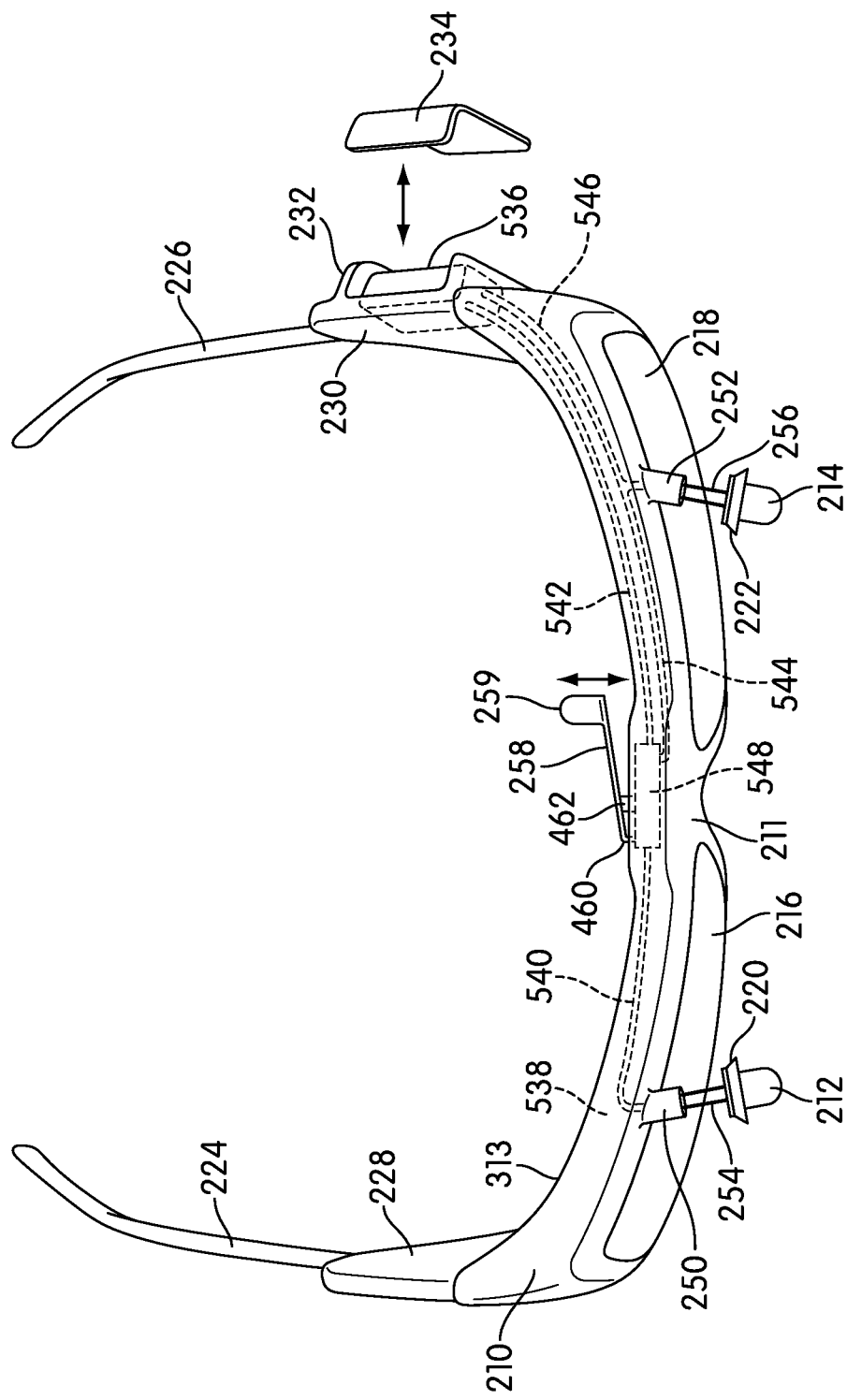
FIG. 5 is a view of the coating inspection device of FIG. 1 with electrical components associated with the ultraviolet light sources shown in hidden lines.

In some embodiments, lever 258 may include a flat spring configured to swing back and forth about pivot point 460 in the direction shown by the arrows in FIGS. 4 and 5. In some embodiments, lever 258 may be biased outwardly in a first position. In some embodiments, lever 258 may be made of a resilient material so that lever 258 may be biased outwardly, as shown in FIGS. 4 and 5. For example, lever 258 may be made from a thin sheet of aluminum, tin, or plastic. When lever 258 is pressed toward frame member 210 to a second position, an actuator nub 462 connected to lever 258 may cause switch 548 to close.

In some embodiments, lever 258 may be positioned on second side 313 of frame member 210 so that a wearer's face may press against nub 259 when wearing coating inspection device 102. Consequently, switch 548 may automatically close when a person puts on coating inspection device 102 and switch 548 may automatically open when a person removes coating inspection device 102. Such an automatic function may eliminate the step of manually turning switch 548 off, which may save energy supplied by the electrical power source. Furthermore, such an automatic function may enhance convenience by reducing the number of steps involved with turning the ultraviolet light source on. In embodiments in which the lenses are ultraviolet resistant lenses, the automatic function may ensure that the wearer's eyes are protected by the lenses before the ultraviolet light sources are turned on.

While lever 258 is shown as being positioned between the lenses in the exemplary embodiment, lever 258 may be positioned in other locations. For example, lever 258 may be positioned on the inside of one of the temple members. The position of lever 258 may be selected based on a variety of factors. For example, in some embodiments, the position of lever 258 may be selected based on the shape of frame member 210 and how frame member 210 contacts a wearer's head. In some embodiments, the position of lever 258 may be selected based on the position of switch 548.

Figure 7:
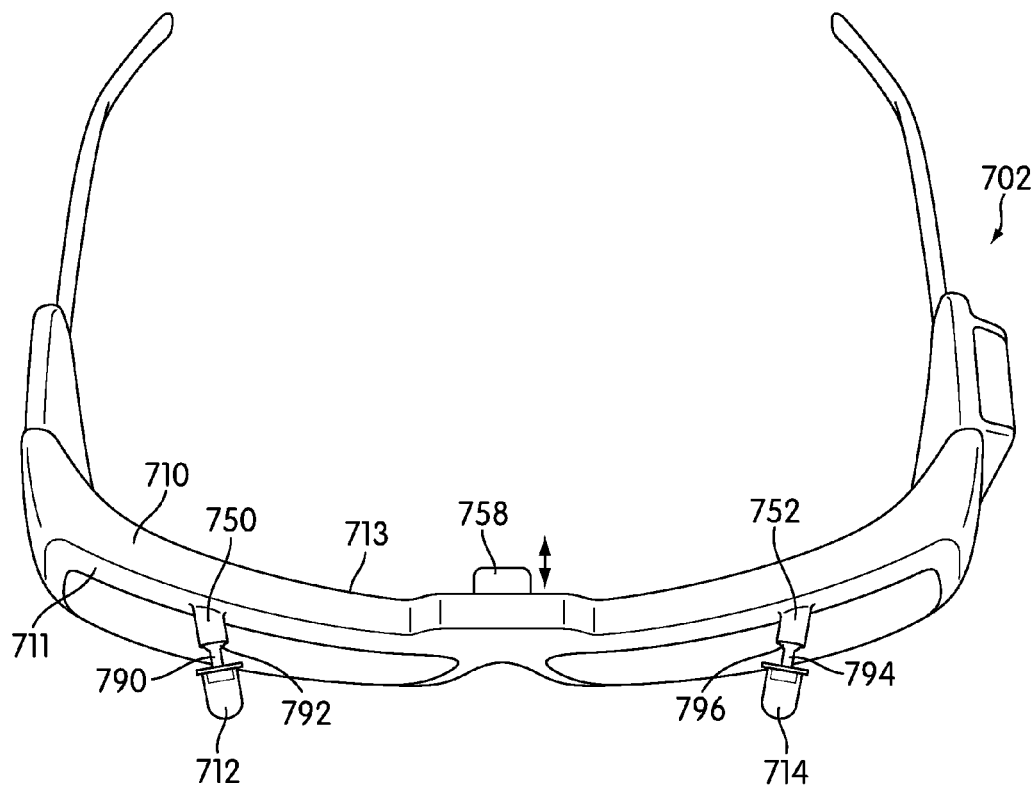
FIG. 7 shows an exemplary embodiment of a coating inspection device.

While a lever 258 is shown in the figures, switch 548 may include other types of actuators. In some embodiments, switch 548 may include another biased type of actuator. For example, the exemplary embodiment shown in FIG. 7 illustrates a resilient button 758. Resilient button 758 may move in the directions shown by the arrows. Resilient button 758 may be biased outwardly in a first position. When resilient button 758 is pressed toward frame member 710 to a second position, an actuator nub 462, shown in FIG. 4, connected to lever 258 may cause switch 548 to close. In some embodiments, switch 548 may include an actuator that is not resilient. For example, switch 548 may include a slidable button that may be manually pushed between open and closed positions. In embodiments in which the actuator is not resilient, the position of the actuator may also be selected based upon the accessibility of the actuator to manually turn the ultraviolet light sources on and off.

Figure 6:
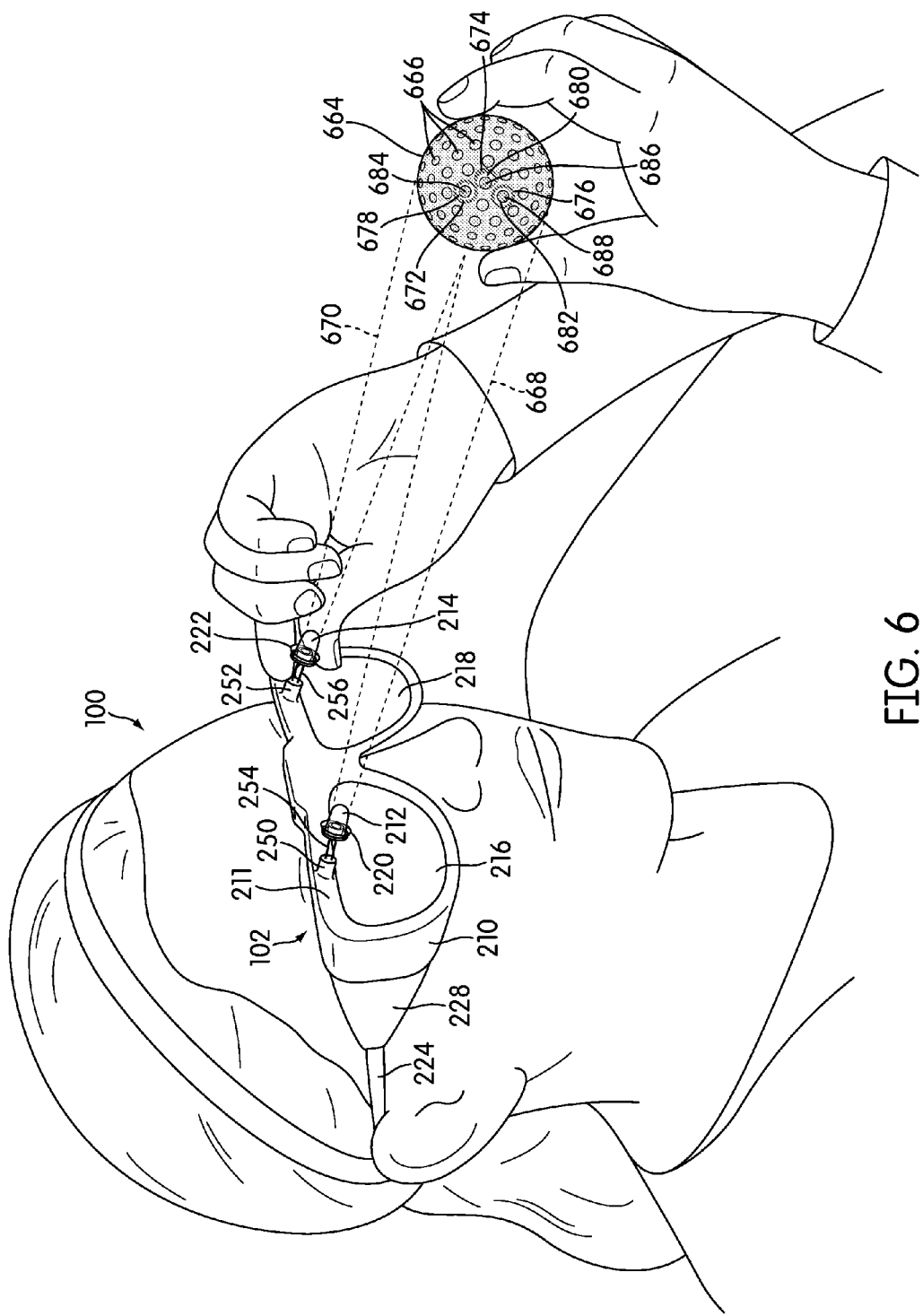
FIG. 6 shows the person from FIG. 1 wearing the coating inspection device of FIG. 1 while inspecting a golf ball.

FIG. 6 shows person 100 wearing coating inspection device 102 while inspecting a golf ball 664 with dimples 666. Ultraviolet rays 668 may be emitted from first ultraviolet light source 212. Ultraviolet rays 670 may be emitted from second ultraviolet light source 214. In some embodiments, the ultraviolet light sources may be disposed on first side 211 of frame member 210. In some embodiments, the ultraviolet light sources may be configured to be moved from a first position in which the ultraviolet light source may be directed at a first angle to the second position in which the ultraviolet light source may be directed at a second angle. In some embodiments, frame member 210 may include features shaped to accommodate electrical components associated with the ultraviolet light sources. For example, in the exemplary embodiment shown in FIGS. 1-6, frame member 210 may include a first protrusion 250 and a second protrusion 252 both extending from first side 211. In some embodiments, first ultraviolet light source 212 may be disposed on first protrusion 250 and second ultraviolet light source 214 may be disposed on second protrusion 252. In some embodiments, the ultraviolet light sources may be associated with frame member 210 so that each ultraviolet light source may be independently adjusted to change the direction in which ultraviolet rays are emitted. In some embodiments, first ultraviolet light source 212 may be connected to frame member 210 at first protrusion 250 by first set of wires 254. In some embodiments, second ultraviolet light source 214 may be connected to frame member 210 at second protrusion 252 by second set of wires 256. In some embodiments, as shown in FIG. 6, second set of wires 256 may be bendable so that the wearer may bend second set of wires 256 to adjust the direction in which ultraviolet rays 670 are emitted. First set of wires 254 may also be bendable so that a wearer may bend first set of wires 254 to adjust the direction in which ultraviolet rays 668 are emitted. Bendable wire may enable the ultraviolet light sources to be positioned in any number of directions. In these embodiments, the ultraviolet light sources may be independently adjusted to change the direction in which ultraviolet rays are emitted. First set of wires 254 and second set of wires 256 may include any number of wires. In some embodiments, the number of wires may be selected based upon a variety of factors. For example, the number of wires may be selected based upon the circuitry used with the ultraviolet light sources.

Figure 8:
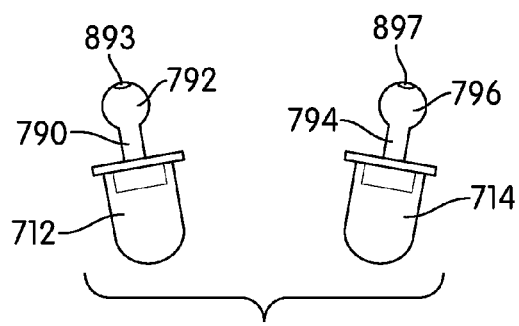
FIG. 8 shows the hinge members of the coating inspection device of FIG. 7.

In some embodiments, mechanisms other than bendable wires may connect the ultraviolet light sources to frame member 210. In some of these embodiments, the mechanisms may be stationary and, in other embodiments, the mechanisms may be moveable to adjust the angle of the ultraviolet light sources. The exemplary embodiment shown in FIGS. 7-8 illustrates a mechanism that may be moveable to adjust the angle of the ultraviolet light sources. As shown in FIG. 7, the ultraviolet light sources may be connected to a frame member 710 by moveable hinge members. A coating inspection device 702 may include frame member 710 having a first side 711 and a second side 713. In some embodiments, a first protrusion 750 and a second protrusion 752 may both extend from first side 711. The hinge member may provide a ball and socket joint, which may enable the ultraviolet light source to be directed in any number of directions. As shown in FIG. 8, first hinge member 790 may include a ball 792 at one end and a first ultraviolet light source 712 at the opposite end. In some embodiments, first protrusion 750 may be configured to receive ball 792. First hinge member 790 may be connected to first side 711 by an opening disposed within first protrusion 750. The opening may have a shape corresponding to the shape of ball 792. Ball 792 may sit inside the opening disposed within first protrusion 750 so that ball 792 may pivot inside first protrusion 750. The wearer may tilt first hinge member 790 so that ball 792 pivots within the opening disposed in first protrusion 750 to adjust the direction in which ultraviolet rays are emitted from first ultraviolet light source 712. In some embodiments, the opening may be disposed on a part of frame member 710 other than the protrusion. As FIG. 8 illustrates, ball 792 may include a hole 893 through which wires may pass to connect with first ultraviolet light source 712 to put first ultraviolet light source 712 in electrical communication with an electrical power source.

A second hinge member 794 may include a ball 796 at one end and a second ultraviolet light source 714 at the opposite end. Second protrusion 752 may be configured to receive ball 796. Second hinge member 794 may be connected to first side 711 by an opening disposed within second protrusion 752. The opening may have a shape corresponding to the shape of ball 796. Ball 796 may sit inside the opening disposed within second protrusion 752 so that ball 796 may pivot inside second protrusion 752. The ball and the opening in the protrusion may provide a ball and socket joint, which may enable the ultraviolet light source to be directed in any number of directions. The wearer may tilt second hinge member 794 to adjust the direction in which ultraviolet rays are emitted from second ultraviolet light source 714. In some embodiments, the opening may be disposed on a part of frame member 710 other than the protrusion. As FIG. 8 illustrates, ball 796 may include a hole 897 through which wires may pass to connect with second ultraviolet light source 714 to put second ultraviolet light source 712 in electrical communication with an electrical power source.

Referring back to FIG. 6, golf ball 664 may be illuminated by the ultraviolet rays emitted by the ultraviolet light sources. The coating material covering golf ball 664 may be ultraviolet reactive. When illuminated by the ultraviolet light sources, the coating material may appear brighter than objects that are not ultraviolet reactive. The thinner the layer of coating material, the dimmer the coating may appear when illuminated by the ultraviolet light sources. After application of coating material, golf ball 664 may have an uneven layer of coating material. In the presence of the ultraviolet light sources, golf ball 664 may appear to be darker in spots where the layer of coating material is thinner. For example, dark spot 672, dark spot 674, and dark spot 676 may indicate regions in which the layer of coating material is thinner. In the presence of ultraviolet light sources, golf ball 664 may appear to be lighter in spots where the layer of coating material is thicker. For example, bright spot 678, bright spot 680, and bright spot 682 may indicate regions in which the layer of coating material is thicker. When golf ball 664 is viewed without ultraviolet illumination, golf ball 664 may appear to be evenly coated with coating material. However, using coating inspection device 102 to illuminate golf ball 664 with ultraviolet light may show the unevenness in the layer of coating material adjacent the edges of dimple 684, dimple 686, and dimple 688.

In some embodiments, during operation, coating inspection device may be placed on a person's face. Referring to FIGS. 1-6, first temple member 224 may rest on one of the person's ears and second temple member 226 may rest on the other ear. Frame member 210 may rest on the person's nose. The person's face may press against an actuator. For example, when using the embodiment of FIGS. 1-6, the person's face may press against nub 259 of lever 258, causing lever 258 to move from the first position, in which switch 548 may be open, to the second position, in which switch 548 may be closed. When switch 548 is closed, first ultraviolet light source 212 and second ultraviolet light source 214 may both be in electrical communication with electrical power source 536. Accordingly, placing coating inspection device 102 on a person's face may turn both first ultraviolet light source 212 and second ultraviolet light source 214 on. The person may view the coating of a golf ball or other object through the lenses. In embodiments in which the lenses are ultraviolet resistant, the person's eyes may be protected by the lenses while wearing coating inspection device 102. Frame member 210 may further protect a wearer's eyes by blocking the ultraviolet light from the wearer's eyes in the spaces surrounding the lenses. In some embodiments, frame member 210 may contact the wearer's face, thereby further shielding the wearer's eyes from the ultraviolet light by blocking the space between the frame member and the wearer's face. In embodiments in which the temple members have shielding portions, the shielding portions may further shield the wearer's eyes from ultraviolet light.

In some embodiments, the wearer may adjust the direction in which the ultraviolet light is emitted by moving the ultraviolet light source from a first position to a second position. For example, when using the embodiment of FIGS. 1-6, a person may bend first set of wires 254 to adjust the position of first ultraviolet light source 212. A person may also bend second set of wires 256 to adjust the position of second ultraviolet light source 214. In another example, when using the embodiment of FIGS. 7-8, a person may tilt first hinge member 790 so that ball 792 pivots within the opening disposed in first protrusion 750 to adjust the direction in which ultraviolet rays are emitted from first ultraviolet light source 712. A person may also tilt second hinge member 794 so that ball 796 pivots within the opening disposed in second protrusion 752 to adjust the direction in which ultraviolet rays are emitted from second ultraviolet light source 714. In some embodiments, the ultraviolet light source may be directed at a first angle in the first position and the ultraviolet light source may be directed at a second angle in the second position.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. An apparatus for inspecting a coating comprising:
    a frame member having a first side and a second side opposite the first side, the frame member being configured to be worn on a person's face with the first side facing away from the person's face and the second side facing toward the person's face and being configured to receive at least one lens;
    at least one lens disposed within the frame member;
    at least one ultraviolet light source disposed on the first side of the frame member; and
    a switch disposed on the frame member, the switch configured to turn on the at least one ultraviolet light source when the frame member is worn by a person and to turn off the at least one ultraviolet light source when the frame member is not worn by a person,
    wherein the switch includes an actuator configured to open and close the switch, the actuator being disposed on the second side of the frame member and configured to be displaced from a first position, in which the switch is open, to a second position, in which the switch is closed, by a person's face pressing against the actuator when the coating inspection device is worn by the person.

2. The apparatus for inspecting a coating according to claim 1, wherein the actuator is closer to the second side in the second position than in the first position.

3. The apparatus for inspecting a coating according to claim 2, wherein the actuator comprises a lever disposed on the second side of the frame member, the lever being configured to be biased outwardly in the first position and to be displaced toward the second side in the second position.

4. The apparatus for inspecting a coating according to claim 2, wherein the actuator comprises a button disposed on the second side, the button being configured to be biased outwardly in the first position and to be displaced toward the second side in the second position.

5. The apparatus for inspecting a coating according to claim 1, wherein the frame member includes a hollow compartment and the switch is disposed within the hollow compartment.

6. The apparatus for inspecting a coating according to claim 1, wherein the at least one ultraviolet light source is disposed on the first side of the frame member above the at least one lens.

7. The apparatus for inspecting a coating according to claim 1, wherein the at least one ultraviolet light source comprises a plurality of ultraviolet light sources.

8. The apparatus for inspecting a coating according to claim 1, wherein the at least one ultraviolet light source is connected to the first side, the at least one ultraviolet light source being movable relative to the frame member such that the at least one ultraviolet light source is configured to be moved from a first position in which the ultraviolet light source is directed at a first angle to the second position in which the ultraviolet light source is directed at a second angle.

9. An apparatus for inspecting a coating comprising:
    a frame member having a first side and a second side opposite the first side, the frame member being configured to be worn on a person's face with the second side facing toward the person's face and configured to receive at least one lens;
    at least one lens disposed within the frame member;
    a first temple member and a second temple member both disposed on the second side of the frame member;
    at least one ultraviolet light source disposed on the first side of the frame member, the at least one ultraviolet light source being movable relative to the frame member such that the at least one ultraviolet light source is configured to be moved from a first position to a second position to adjust the direction in which the at least one ultraviolet light source is directed; and
    electrical components associated with the at least one ultraviolet light source.

10. The apparatus for inspecting a coating according to claim 9, wherein the at least one ultraviolet light source comprises a plurality of ultraviolet light sources each configured to be independently moved relative to the frame member to direct light in a plurality of directions.

11. The apparatus for inspecting a coating according to claim 9, wherein the at least one ultraviolet light source is connected to the frame member by a wire, the wire being configured to be bent to move the at least one ultraviolet light source from the first position in which the ultraviolet light source is directed at a first angle with respect to the frame member to the second position in which the ultraviolet light source is directed at a second angle with respect to the frame member.

12. The apparatus for inspecting a coating according to claim 9, wherein the at least one ultraviolet light source is connected to the frame member by a hinged member, the hinged member being configured to pivot with respect to the first side to move the at least one ultraviolet light source from the first position in which the ultraviolet light source is directed at a first angle to the second position in which the ultraviolet light source is directed at a second angle.

13. The apparatus for inspecting a coating according to claim 12, the hinged member including a ball disposed within an opening in the frame member, the ball being configured to pivot within the opening.

14. The apparatus for inspecting a coating according to claim 9, wherein the frame member includes a hollow compartment configured to house the electrical components.

15. The apparatus for inspecting a coating according to claim 9, wherein the at least one lens is an ultraviolet resistant lens.

16. The apparatus for inspecting a coating according to claim 9, the first temple member includes a shielding portion proximate the second side.

17. The apparatus for inspecting a coating according to claim 9, further comprising a switch disposed on the frame member, the switch configured to turn on the at least one ultraviolet light source when the frame member is worn on the person's face and to turn off the at least one ultraviolet light source when the frame member is removed from the person's face.

18. A method of inspecting a coating on a golf ball, comprising:
  turning on at least one ultraviolet light source extending from a first side of a frame member of a coating inspection device by placing the coating inspection device on a person's face such that the person's face presses against and moves an actuator disposed on a second side of the frame member that is opposite the first side, wherein the coating inspection device includes at least one lens disposed within the frame member; and
  viewing a golf ball through the at least one lens while the ultraviolet light source is on.

19. The method of inspecting a coating on a golf ball according to claim 18, further comprising:
  adjusting the direction in which ultraviolet light is emitted from the ultraviolet light source by moving the ultraviolet light source relative to the frame member from a first position to a second position.

20. The method of inspecting a coating on a golf ball according to claim 19, wherein the ultraviolet light source is directed at a first angle with respect to the frame member in the first position and the ultraviolet light source is directed at a second angle with respect to the frame member in the second position.

21. The method of inspecting a coating on a golf ball according to claim 18, wherein the step of turning on the at least one ultraviolet light source includes pressing an actuator toward the second side with the person's face.

\* \* \* \* \*